(12) United States Patent
Jun et al.

(10) Patent No.: US 6,291,716 B1
(45) Date of Patent: Sep. 18, 2001

(54) ORTHO-ALKYLATION METHOD OF AROMATIC KETONES

(75) Inventors: Chul Ho Jun, 103-1203 Doklipmoon Samho Apt., Youngchon-dong 100, Seodaemoon-ku Seoul; Jun Bae Hong, Kyunggi-do; Kwan Yong Chung, Seoul; Yeon Hee Kim, Inchon-si, all of (KR)

(73) Assignee: Chul Ho Jun, Seoul (KR)

( * ) Notice: Subject to any disclaimer, the term of this patent is extended or adjusted under 35 U.S.C. 154(b) by 0 days.

(21) Appl. No.: 09/792,108

(22) Filed: Feb. 26, 2001

(51) Int. Cl.$^7$ .................................................... C07C 45/68

(52) U.S. Cl. ............................................. 568/312; 568/317

(58) Field of Search ...................................... 568/312, 317

(56) References Cited

U.S. PATENT DOCUMENTS 5,396,011 * 3/1995 Kuhn .
6,072,073 * 6/2000 Kawatsura et al. .

* cited by examiner

Primary Examiner—Sreeni Padmanabhan
Assistant Examiner—Sikarl A. Witherspoon
(74) Attorney, Agent, or Firm—Harrison & Egbert

(57) ABSTRACT

An ortho-alkylation method of an aromatic ketone. In the method, as starting materials, the aromatic ketone is reacted with aliphatic or aromatic alkyl moiety-containing olefins in the presence of a primary amine and a transition metal catalyst as reaction catalysts, or ketimines resulting from a reaction of aromatic ketones with a primary amine are reacted with aliphatic or aromatic alkyl moiety-containing olefins in the presence of a transition metal catalyst, thereby introducing the alkyl moiety to the ortho-position of the aromatic ketone.

4 Claims, No Drawings

ORTHO-ALKYLATION METHOD OF AROMATIC KETONES

BACKGROUND OF THE INVENTION

1. Field of the Invention

The present invention relates, in general, to an ortho-alkylation method of an aromatic ketone and, more particularly, to a method for introducing an alkyl moiety to an ortho-position of an aromatic ketone by reacting the ketones with olefins in the presence of an amine catalyst and a transition metal catalyst.

2. Description of Related Art

Until now, the introduction of substituents to aromatic compounds has been carried out depending on ortho and para-directivity of conventional substituents. However, it is difficult to introduce a new substituent to ortho-position of compounds because of their steric hindrance, as it is. Further, in a general organic synthesis, functional groups cannot be selectively attached to the ortho-position of aromatic compounds. Additionally, a Fridel-Craft alkylation of aromatic compounds has the same limitation as described above.

Ortho-alkylation through a homogeneous catalyst reaction was first studied by Professor S. Murai, Japan, wherein alkyl groups were introduced to ortho-position of aromatic ketones by reacting the ketones with a silane group-containing olefins in the presence of a ruthenium catalyst. However, this method suffers from the disadvantages of having high efficiency for only silane-containing olefins, and low efficiency or no reactivity for general alkyl moiety-containing olefins, internal olefins or diene compounds.

BRIEF SUMMARY OF THE INVENTION

Therefore, it is an object of the present invention to overcome the above problems encountered in the prior art and to provide a method for introducing an alkyl moiety to an ortho-position of an aromatic ketone through the reaction of the aromatic ketone with an aliphatic or aromatic alkyl moiety-containing compound.

In accordance with an embodiment of the present invention, there is an ortho-alkylation method of an aromatic ketone, in which an alkyl moiety is introduced to an ortho-position of the aromatic ketone in the presence of a primary amine and a transition metal catalyst, said alkyl moiety compound being sourced from aliphatic or aromatic olefins, internal olefins or diene compounds.

In accordance with another embodiment of the present invention, there is an ortho-alkylation method of an aromatic ketone, in which the aromatic ketone is reacted with a primary amine to produce a ketimine which is then reacted with an aliphatic or aromatic alkyl moiety-containing compound in the presence of a transition metal catalyst to introduce an alkyl moiety to an ortho-position of the ketone, said aliphatic or aromatic alkyl moiety-containing compound being sourced from olefins, internal olefins or diene compounds.

DETAILED DESCRIPTION OF THE INVENTION

Useful as starting materials in the present invention are aromatic ketones such as acetophenone or benzophenone, ketimines resulting from the condensation of the aromatic ketones with a primary amine, and olefins such as an aliphatic and aromatic alkyl-containing olefin, internal olefins in which a double bond is internally contained, or diene compounds having two double bonds.

When aromatic ketones are used as starting materials, a primary amine and a transition metal catalyst are employed together as reaction catalysts. At that time, alkylation is carried out in the presence of the transition metal catalysts as illustrated in the following chemical reaction formula 1.

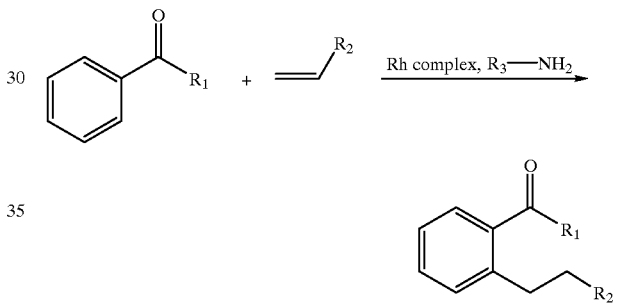

(wherein, $R_1$ is an alkyl group, $R_2$ is an alkyl or alkenyl group and $R_3$ is an alkyl or aryl group.)

In the case of using ketimine resulting from the condensation of an aromatic ketone with a primary amine as starting materials, only a transition metal catalyst is added to carry out alkylation.

A mechanism for introducing an alkyl moiety to an ortho-position of ketones through the reaction of a ketone or ketimine with olefins is shown in the following reaction formula 2.

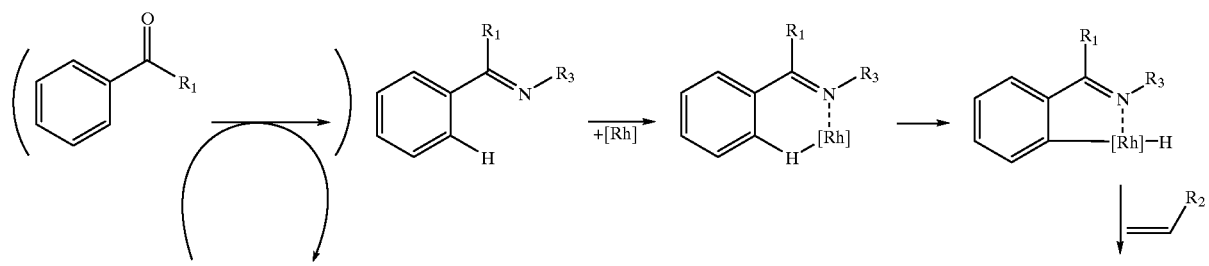

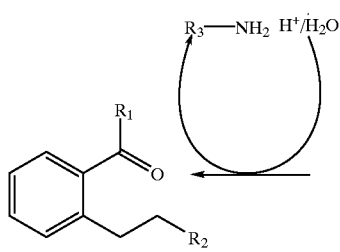

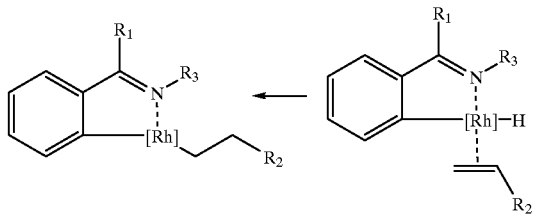

-continued (wherein, $R_1$ is an alkyl group, $R_2$ is an alkyl or alkenyl group, $R_3$ is an alkyl or aryl group, and [Rh] is a rhodium monovalent catalyst.)

A transition metal catalyst (eg., rhodium monovalent catalyst) is coordinated to nitrogen in ketimine to cleave an adjacent carbon-hydrogen bond, thereby forming an intermediate of a stable pentagonal ring structure to which olefins are coordinated to produce ketimine having substituted alkyl group at an ortho-position through the hydride-insertion and then the reductive-elimination. Such ketimine is hydrolyzed with water to afford aromatic ketone having a substituted alkyl group at its ortho-position.

Examples of transition metal catalysts suitable for the present invention are selected from the group consisting of rhodium monovalent catalysts such as $[Rh(C_8H_{14})_2Cl]_2$, rhodium trivalent catalyst such as $[RhCl_3AH_2O]$, Wilkins catalysts such as $(PPh_3)_3RhCl$ or mixtures thereof. When rhodium monovalent or trivalent catalysts are employed, a phosphine compound, such as triphenyl phosphine ($PPh_3$), is preferably added. Primary amines are exemplified by benzylamine, aniline, cyclohexylamine, and tert-butylamine.

It is more efficient that said materials are dissolved in organic solvents, such as toluene, and then reacted. The reaction is preferably conducted at approximately 100–150° C. for 2–4 hours.

A better understanding of the present invention may be obtained in light of the following examples which are set forth to illustrate, but are not to be construed to limit the present invention.

EXAMPLE 1

In a 500 ml pressure reactor, N-benzyl-(1-phenylethylidene)-amine 68 mg (0.32 mmol), tristriphenylphosphine rhodium (I) chloride 6 mg (0.0065 mmol), 3,3-dimethyl-1-butene 27 mg (0.32 mmol) were placed and dissolved in toluene 100 mg. While the reactor was stopped with a stopper, the reactants were heated at 150° C. for 2 hours with stirring. After completion of the reaction, the reactant mixture was dissolved in THF 3 ml and then combined with 1 N HCl soln. 10 ml, followed by hydrolysis with stirring for 12 hours at room temperature. After the mixture was three times extracted with $Et_2O$ and $CH_2Cl_2$, the organic layer was dried over $MgSO_4$ and then filtered and the solvent was evaporated under reduced pressure. The reactant mixture of the organic layer was purified by column chromatography on silica gel (5:2 hexane:ethyl acetate) to obtain 2-(3,3-dimethylbutyl)phenyl-1-ethanone 64 mg (0.31 mmol). Yield: 97%. Under the same conditions, a variety of olefins were employed, and the results are given in Table 1, below.

TABLE 1

| Olefins | Products | Yield (%) | Note |
|---|---|---|---|
| 3,3-dimethyl-1-butene | [structure: ortho-substituted acetophenone with $(CH_3)_3$] | 97 | |
| 1-hexene | [structure with $n\text{-}C_4H_9$] | 94 | 1-hexene 1.6 mmol |
| 1,2,3,4,5-pentafluorostyrene | [structure with $C_6F_5$] | 91 | |
| Vinylcyclohexane | [structure with Cy] | 68 | |
| 1-octene | [structure with $n\text{-}C_6H_{13}$] | 71 | 1-octene 1.6 mmol |
| 1-dodecene | [structure with $n\text{-}C_{10}H_{21}$] | 82 | 1-dodecene 1.6 mmol |
| Trimethylvinylsilane | [structure with $CH_2CH_3$ and $Si(CH_3)_3$] | 96 | |

TABLE 1-continued

| Olefins | Products | Yield (%) | Note |
|---|---|---|---|
| Styrene | 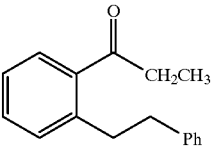 | 41 | |
| Norbornene | 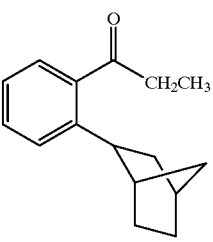 | 92 | |
| 2-pentene | 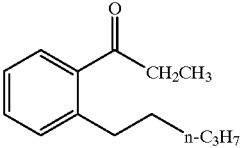 | 95 | 1-pentene 1.6 mmol |
| 2-hexane | 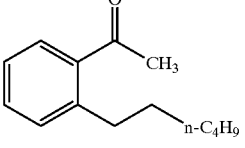 | 42 | 1-hexene 1.6 mmol |

In a 500 ml pressure reactor, N-phenyl-(1-phenylethylidene)-amine 63 mg (0.32 mmol), tristriphenylphosphine rhodium (I) chloride 6 mg (0.0065 mmol) and 3,3-dimethyl-1-butene 27 mg (0.32 mmol) were placed and dissolved in toluene 100 mg. While the reactor was stopped with a stopper, the reactants were heated at 150° C. for 2 hours with stirring. After completion of the reaction, the reactant mixture was dissolved in THF 3 ml and then combined with 1 N HCl soln. 10 ml, followed by hydrolysis with stirring for 12 hours at room temperature. After the mixture was three times extracted with $Et_2O$ and $CH_2Cl_2$, the organic layer was dried over $MgSO_4$ and then filtered, and the solvent was evaporated under reduced pressure. The reactant mixture of the organic layer was purified by column chromatography on silica gel (5:2 hexane:ethyl acetate) to obtain 2-(3,3-dimethylbutyl)phenyl-1-ethanone 56 mg (0.27 mmol). Yield: 85%. Under the same conditions, various ketamines were employed. The results are given in Table 2, below.

TABLE 2

| Nos. | Ketimine (Reactant) | Yield (%) |
|---|---|---|
| 1 | 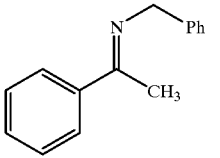 | 97 |
| 2 | 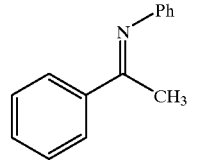 | 85 |
| 3 | 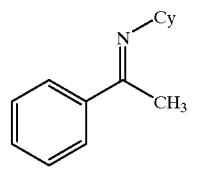 | 83 |
| 4 | 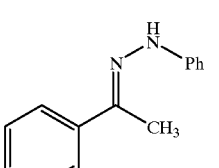 | 7 |

EXAMPLE 3

This example was carried out in the same manner as in Example 1, except that ketimine compounds 0.32 mmol as shown in the following table 3 and trimethylvinylsilane 32 mg (0.32 mmol) were used. The results are presented in Table 3, below.

TABLE 3

| Nos. | Ketimine | Products and Yields |
|---|---|---|
| 1 | 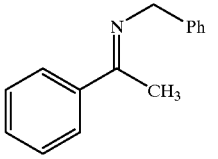 | 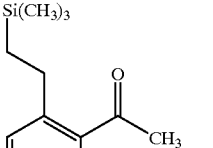 92% |

TABLE 3-continued

| Nos. | Ketimine | Products and Yields | |
|---|---|---|---|
| 2 | N-benzyl-(1-phenylpropylidene)-amine | 2-(2-trimethylsilylethyl)phenyl ethyl ketone, 81% | 2,6-bis(2-trimethylsilylethyl)phenyl ethyl ketone, 12% |
| 3 | N-benzyl-(1-phenylbutylidene)-amine | 2-(2-trimethylsilylethyl)phenyl propyl ketone, 79% | 2,6-bis(2-trimethylsilylethyl)phenyl propyl ketone, 12% |
| 4 | N-benzyl-(1-phenylpentylidene)-amine | 2-(2-trimethylsilylethyl)phenyl butyl ketone, 82% | 2,6-bis(2-trimethylsilylethyl)phenyl butyl ketone, 9% |
| 5 | N-benzyl-(1-phenylhexylidene)-amine | 2-(2-trimethylsilylethyl)phenyl pentyl ketone, 57% | 2,6-bis(2-trimethylsilylethyl)phenyl pentyl ketone, 16% |

EXAMPLE 4

In a 500 ml pressure reactor, N-benzyl-(1-phenylethylidene)-amine 68 mg (0.32 mmol), tristriphenylphosphine rhodium (I) chloride 6 mg (0.0065 mmol) and diene 3.24 mmol were placed and dissolved in toluene 100 mg. While the reactor was stopped with a stopper, the reactants were heated at 150° C. for 2 hours with stirring. After completion of the reaction, the reactant mixture was dissolved in THF 3 ml and then combined with 1 N HCl soln. 10 ml, followed by hydrolysis with stirring for 12 hours at room temperature. After the mixture was three times extracted with $Et_2O$ and $CH_2Cl_2$, the organic layer was dried over $MgSO_4$ and then filtered, and the solvent was evaporated under reduced pressure. Unsaturated groups in the reactant mixture were reduced in the presence of hydrogen and Pd/C. The reactant mixture was purified by column chromatography on silica gel (5:2 hexane:ethyl acetate) to obtain ketones with yields as shown in the following table 4. Under the same conditions, various dienes were employed, and the results are given in Table 4, below.

TABLE 4

| Nos. | Diene | Product | Yield (%) |
|---|---|---|---|
| 1 | CH₂=CH-(CH₂)₂-CH=CH₂ | 2-acetyl-phenyl with (CH₂)₂-CH=CH₂ chain | 92 |
| 2 | CH₂=CH-(CH₂)₄-CH=CH₂ | 2-acetyl-phenyl with (CH₂)₄-CH=CH₂ chain | 97 |
| 3 | CH₂=CH-(CH₂)₆-CH=CH₂ | 2-acetyl-phenyl with (CH₂)₆-CH=CH₂ chain | 92 |

EXAMPLE 5

This example was conducted in the same manner as in Example 1, except that reaction temperatures were changed. The results are given in Table 5, below.

TABLE 5

Product: 2-(3,3-dimethylbutyl)phenyl-1-ethanone (t-C₄H₉)

| Nos. | Temp. (° C.) | GC Yield (%) |
|---|---|---|
| 1 | 80 | 12 |
| 2 | 100 | 53 |
| 3 | 130 | 81 |
| 4 | 150 | 86 |
| 5 | 170 | 83 |

EXAMPLE 6

In a 500 ml pressure reactor, acetophenone 26 mg (0.22 mmol), benzylamine 12 mg (0.11 mmol), tristriphenylphosphine rhodium (I) chloride 10.0 mg (0.011 mmol) and 3,3-dimethyl-1-butene 91 mg (1.1 mmol) were placed and dissolved in toluene 50 mg. While the reactor was stopped with a stopper, the reactants were heated at 150° C. for 2 hours with stirring. After completion of the reaction, 2-(3,3-dimethylbutylphenyl)-1-ethanone was found to be obtained at a yield of 85% as measured by gas chromatography. Under the same conditions, molar fractions of benzylamines were changed. The results are given in Table 6, below.

TABLE 6

Product: 2-(3,3-dimethylbutyl)phenyl-1-ethanone (t-C₄H₉)

| Nos. | Amount of combined benzylamine (mol %) | GC Yield (%) | Notes |
|---|---|---|---|
| 1 | 0 | 0 | |
| 2 | 30 | 43 | |
| 3 | 40 | 72 | |
| 4 | 50 | 85 | Including 7% di-alkylation products |
| 5 | 60 | 29 | |
| 6 | 70 | 33 | |
| 7 | 100 | 27 | |

EXAMPLE 7

In a 500 ml pressure reactor, acetophenone 26 mg (0.22 mmol), benzylamine 12 mg (0.11 mmol), tristriphenylphosphine rhodium (I) chloride 10.0 mg (0.011 mmol) and 3,3-dimethyl-1-butene 91 mg (1.1 mmol) were placed. While the reactor was stopped with a stopper, the reactants were heated at 150° C. for 6 hours with stirring. After completion of the on, a reactant mixture was dissolved in THF 3 ml and added with 1 N HCl soln. 10 ml, followed by hydrolysis with stirring for 12 hours at room temperature. After the mixture was two or three times extracted with Et₂O and CH₂Cl₂, the organic layer was dried over MgSO₄ and then filtered, and the solvent was evaporated under reduced pressure. The reactant mixture of the organic layer was purified by column chromatography on silica gel (5:2 hexane:ethyl acetate) to obtain 2-(3,3-dimethylbutyl)phenyl-1-ethanone 42 mg (0.21 mmol). Yield: 95%. Under the same conditions, various olefins were employed, and the results are given in Table 7, below.

TABLE 7

| Olefin | Product | Yield (%) |
|---|---|---|
| 3,3-dimethyl-1-butene | 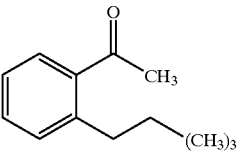 | 95 |
| 1-hexene | 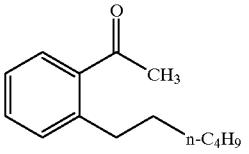 | 72 |
| 1,2,3,4,5-pentafluorostyrene | 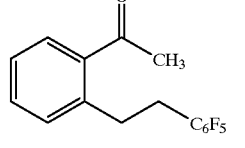 | 68 |
| Vinylcyclohexane | 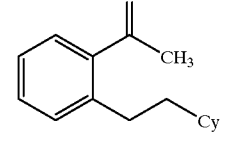 | 89 |
| 1-octene | 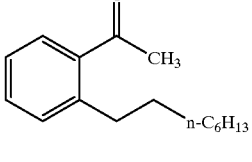 | 15 |
| 1-dodecene | 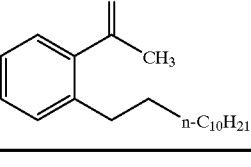 | 17 |

EXAMPLE 8

This example was performed in the same manner as in Example 7, except that ketone as shown in the following table 8, 0.22 mmol and 3,3-dimethyl-1-butene 91 mg (1.1 mmol) were used. The results are given in Table 8, below.

TABLE 8

| Ketone | Product | Yield (%) |
|---|---|---|
| 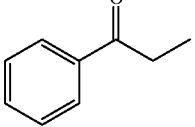 | 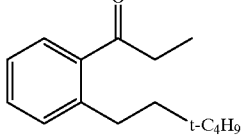 | 86 |
| 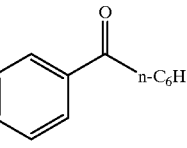 | 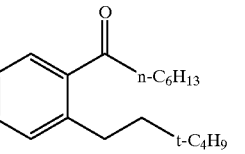 | 72 |
| 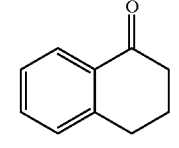 | 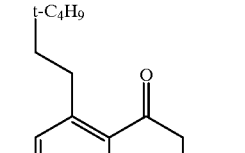 | 87 |

As shown in the above examples, the method of the present invention has high selectivity and reactivity relative to conventional olefins with very low reactivity, such as internal olefins or dienes as well as common alkyl-containing olefins. Accordingly, the ortho-alkylation method of ketones can be used in organic synthesis fields including the synthesis of natural materials or new materials.

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

What is claimed is:

1. An ortho-alkylation method of an aromatic ketone, comprising introducing an alkyl moiety to an ortho-position of the aromatic ketone in the presence of a primary amine and a transition metal catalyst, said alkyl moiety compound being sourced from aliphatic or aromatic olefins, internal olefins or diene compounds.

2. An ortho-alkylation method of an aromatic ketone, comprising reacting an aromatic ketone with a primary amine to produce a ketimine which is then reacted with an aliphatic or aromatic alkyl moiety-containing compound in the presence of a transition metal catalyst to introduce an alkyl moiety to an ortho-position of the ketone, said aliphatic or aromatic alkyl moiety-containing compound being sourced from olefins, internal olefins or diene compounds.

3. The method as set forth in claim 1, wherein said transition metal catalyst is any one selected from the group consisting of rhodium monovalent compounds, phosphine-added rhodium monovalent compounds, rhodium trivalent compounds, phosphine-added rhodium trivalent compounds, and Wilkinsons compounds.

4. The method as set forth in claim 1, wherein said primary amine is selected from the group consisting of benzylamine, aniline, and cyclohexylamine.

* * * * *